United States Patent [19]

Bronstein et al.

[11] Patent Number: 5,582,980
[45] Date of Patent: *Dec. 10, 1996

[54] CHEMILUMINESCENT 1,2-DIOXETANES

[75] Inventors: Irena Bronstein; Brooks Edwards, both of Newton; Alison Sparks, North Andover, all of Mass.

[73] Assignee: Tropix, Inc., Bedford, Mass.

[*] Notice: The term of this patent shall not extend beyond the expiration date of Pat. No. 5,326,892.

[21] Appl. No.: 231,673

[22] Filed: Apr. 25, 1994

Related U.S. Application Data

[63] Continuation-in-part of Ser. No. 57,903, May 7, 1993, which is a continuation-in-part of Ser. No. 806,925, Dec. 11, 1991, abandoned, which is a division of Ser. No. 574,786, Aug. 30, 1990, Pat. No. 5,112,960, which is a continuation-in-part of Ser. No. 559,152, Jul. 25, 1990, abandoned, which is a division of Ser. No. 367,772, Jul. 17, 1989, abandoned.

[51] Int. Cl.$^6$ .................. C12Q 1/00; C12Q 1/68; G01N 33/53; C07H 15/24
[52] U.S. Cl. .................. 435/6; 435/4; 435/810; 435/975; 536/18.1; 536/26.21; 536/26.23; 536/26.7; 536/26.26; 536/27.13; 549/330; 549/332
[58] Field of Search .................. 435/6, 4, 810, 435/975; 536/18.1, 26.21, 26.23, 26.7, 26.26, 27.13; 549/332, 330

[56] References Cited

U.S. PATENT DOCUMENTS

| | | | |
|---|---|---|---|
| 4,931,223 | 6/1990 | Bronstein et al. | 435/4 |
| 4,952,707 | 8/1990 | Edwards et al. | 435/4 |
| 4,983,779 | 1/1991 | Schaap | 435/6 |
| 5,132,204 | 7/1992 | Urdea et al. | 435/4 |
| 5,145,772 | 9/1992 | Voyta et al. | 435/4 |
| 5,326,882 | 7/1994 | Bronstein et al. | 549/16 |

FOREIGN PATENT DOCUMENTS

92/04341  3/1992  WIPO.

OTHER PUBLICATIONS

Chemical Abstract, vol. 117, AN 107794, WO 92/04341, Mar. 19, 1992.

*Primary Examiner*—Douglas W. Robinson
*Assistant Examiner*—Louise N. Leary
*Attorney, Agent, or Firm*—Oblon, Spivak, McClelland, Maier & Neustadt, P.C.

[57] ABSTRACT

Spiroadamantyl dioxetanes bearing an alkoxy substituent, and a phenyl substituted on the dioxetane ring can be activated to chemiluminesce if the aromatic substituent bears a meta-substituted moiety designated OX, wherein the X is cleaved by an enzyme with which the dioxetane is permitted to come in contact with. The $T_{1/2}$ kinetics of the chemiluminescent reaction, as well as the signal intensity and/or quantum yield of the chemiluminescent reaction, can be altered by addition of a chlorine substituent at position 4 on the phenyl ring. Signal strength can further be enhanced by recognized chemiluminescent enhancers.

6 Claims, 9 Drawing Sheets

CHEMILUMINESCENT 1,2-DIOXETANES

This application is CIP of copending U.S. application Ser. No. 08/057,903, filed May 7, 1993 which is incorporated herein by reference, which is a CIP of U.S. application Ser. No. 07/806,925 filed Dec. 11, 1991, now abandoned, which is in turn a divisional application of U.S. application Ser. No. 07/574,786 filed Aug. 30, 1990 now U.S. Pat. No. 5,112,960, a CIP of U.S. application Ser. No. 07/559,152 filed Jul. 25, 1990, now abandoned, itself a divisional application of U.S. application Ser. No. 07/367,772 filed Jul. 17, 1989, now abandoned.

BACKGROUND OF THE INVENTION

1. Field of the Invention

This invention pertains to a chemiluminescent 1,2-dioxetane derivative which can be enzymatically activated to decompose and, through decomposition, release light. The dioxetane is particularly characterized by the presence of a phenyl ring bonded to the dioxetane, which ring bears a meta-substituted enzymatically cleavable group, which when cleaved, leaves the phenoxyanion of the dioxetane, and, at the four position, an electron withdrawing chlorine group. By selecting the identity of the substituent at the four position particular aspects of the chemiluminescent properties of the dioxetane, including half life, quantum yield, S/N ratio, etc., can be altered.

2. Background of the Invention 1,2-dioxetane enzyme substrates have been well established as highly efficient chemiluminescent reporter molecules for use in enzyme immunoassays of a wide variety of types. These assays provide a preferred alternative to conventional assays that rely on radioisotopes, fluorophores, complicated color shifting, secondary reactions and the like. Dioxetanes developed for this purpose include those disclosed in U.S. Pat. No. 4,978,614 as well as U.S. Pat. No. 5,112,960. U.S. Pat. No. 4,978,614 discloses, among others, 3-(2'-spiroadamantane)4-methoxy-4-(3"-phosphoryloxy)phenyl-1,2-dioxetane, which has received world-wide attention, and is commercially available under the trade name AMPPD. U.S. Pat. No. 5,112,960, discloses dioxetane compounds, wherein the adamantyl stabilizing ring is substituted, at either bridgehead position, with a variety of substituents, including hydroxy, halogen, and the like, which convert the otherwise static or passive adamantyl stabilizing group into an active group involved in the kinetics of decomposition of the dioxetane ring. Compounds of this type have similarly received international attention, giving a faster and stronger signal than AMPPD in many applications. CSPD is a spiroadamantyl dioxetane phenyl phosphate with a chlorine substituent on the adamantyl group, and, like AMPPD, is available from Tropix, Inc. of Bedford, Mass.

Compounds of this type have been particularly developed for enhanced sensitivity in assays for the presence of analytes in concentrations as low as $10^{-12}$M and lower. In certain applications, compounds of this type are used in conjunction with enhancers to detect analytes in concentration of $10^{-12}$M or lower. These enhancement agents, which include natural and synthetic water-soluble macromolecules, are disclosed in detail in U.S. Pat. No. 5,145,772. Preferred enhancement agents include water-soluble polymeric quaternary ammonium salts, such as poly(vinylbenzyltrimethylammonium chloride) (TMQ), poly(vinylbenzyltributylammonium chloride) (TBQ) and poly(vinylbenzyldimethylbenzylammonium chloride) (BDMQ).

These enhancement agents improve the chemiluminescent signal of the dioxetane reporter molecules, apparently by providing a hydrophobic environment in which the dioxetane is sequestered. Water, an unavoidable aspect of most assays, due to the use of body fluids, is a natural "quencher" of the dioxetane chemiluminescence. The enhancement molecules apparently exclude water from the microenvironment in which the dioxetane molecules, or at least the excited state emitter species reside, resulting in enhanced chemiluminescence. Other effects associated with the enhancer-dioxetane interaction could also contribute to the chemiluminescence enhancement.

Additional advantages can be secured by the use of selected membranes, including nylon membranes and treated nitrocellulose, providing a similarly hydrophobic surface for membrane-based assays, and other membranes coated with the enhancer-type polymers described.

Nonetheless, it remains a general goal of the industry to improve the performance of these stabilized, chemiluminescent dioxetane reporter molecules, to improve the machine readability, sensitivity, and performance aspects of the immunoassays, dependent on the chemiluminescent signal released by the dioxetanes.

By way of background, and as disclosed in all the patents referenced above, the enzymatically-activated dioxetanes are used as reporter molecules, as substrates for enzymes which cleave the enzyme-labile group bonded to an aromatic substituent on the dioxetane ring. Thus, the enzyme, e.g., alkaline phosphatase is either present alone or covalently linked or otherwise complexed with either an antigen or antibody, in conventional antigen/antibody ligand binding assays, or a nucleic acid probe in nucleic acid assays. The enzyme-bearing antigen or antibody, or nucleic acid probe, is then admixed with the analyte suspected of containing the target antigen, or nucleic acid sequence, under conditions which permit complexing or hybridization between the antigen/antibody or probe/nucleic acid sequence. After washing away or separating off all noncomplexed or nonhybridized material, the dioxetane substrate is added. If the suspected analyte is present, the enzyme will cleave the enzyme-labile group on the aromatic substituent on the dioxetane, e.g., phenyl or naphthyl, yielding the phenoxy or naphthyloxy anion intermediate. This anion decomposes, by electron transfer through the aromatic ring, cleaving the dioxetane ring, and yielding two carbonyl-based products. The cleavage/decomposition event is the light-releasing event.

To automate clinical assays, and to provide for substantial throughput, continued reductions in the halflife, or $T_{1/2}$ of the dioxetane, as well as a reduction in the amount of time required to reach the maximum emission of light of the reporter molecule, is desirable. At the same time, to detect analytes in extremely low concentrations, below, e.g., about $10^{-12}$M, it is desirable to improve the intensity of the signal of the dioxetane reporter molecule, and simultaneously desirable to avoid increasing the background noise due to nonenzymatically-induced light release, so as to improve the overall sensitivity of the assay. Thus, further improvements in chemiluminescent dioxetane reporter molecules are sought.

SUMMARY OF THE INVENTION

The above goals, and others, are met by a new dioxetane, particularly characterized by a substituent on the aromatic ring bonded to the dioxetane, in addition to the meta-substituted enzyme-labile group. Thus, the novel dioxetane of this invention has the general structure below.

wherein R is an alkyl of 1–3 carbon atoms and wherein X is an enzyme cleavable group selected from the group consisting of a phosphate, galactoside, acetate, 1-phospho-2,3-diacylglyceride, 1-thio-D-glucoside, adenosine triphosphate, adenosine diphosphate, adenosine monophosphate, adenosine, α-D-glucoside, β-D-glucoside, β-D-glucuronide, α-D-mannoside, β-D-mannoside, β-D-fructofuranoside, β-glucosiduranate, P-toluenesulfonyl-L-arginine ester, and P-toluenesulfonyl-L-arginine amide.

BRIEF DESCRIPTION OF THE DRAWINGS

FIG. 2 reflects the presence of a chemiluminescence enhancer, polyvinylbenzyltributylammonium chloride.

DETAILED DESCRIPTION OF THE INVENTION

Among other inventive compounds within the structure of formula I, a particularly preferred compound has the structure:

The name of this compound is disodium 2-chloro-5-(4-methoxyspiro[1,2-dioxetane-3,2'-(5-chloro-)tricyclo[3,3,1-1$^{3,7}$]-decan]-1-yl)-1-phenyl phosphate.

This compound is generally referred to as CDP-Star. It can be synthesized as shown in the following reaction scheme.

& isomer

4-Chloro-3-methyoxybenzaldehyde dimethyl acetal 3

A heterogenous mixture of methanol (2 ml), CH$_2$Cl$_2$ (3 ml), 4-chloro-3-methoxybenzaldehyde (2 g, 11.7 mmol; prepared essentially as described by R. M. Riggs et al., J. Med. Chem., 30 1887, 1987.), trimethyl orthoformate (1.7 ml, 15.5 mmol) and a large crystal of p-toluenesulfonic acid was stirred at room temperature for one hour. Additional MeOH (1 ml) and a crystal of p-toluenesulfonic acid were added and the solution was warmed until homogenous. Upon completion of the reaction, the solution was stirred 5 min with excess solid NaHCO$_3$ and rotory evaporated to remove solvents. The paste was dissolved in 40 ml EtOAC, partitioned against dilute NaHCO$_3$ solution, and evaporated to yield a light brown oil. The reaction was repeated with another 2 g of 4-Chloro-3-methyoxybenzaldehyde and both product oils were combined to give 4.37 g (86%) of dimethyl acetal 3.

IR (neat, cm$^{-1}$): 2930, 2810, 1582, 1580, 1483, 1460, 1402, 1348, 1268, 1100, 1059, 989, 861, 827, 790.

$^1$H NMR (CDCl3, ppm): 3.30 (6H, s), 3.90 (3H, s), 5.33 (1H, s), 6.95 (1H, d), 7.03 (1H, s), 7.32 (1H, d).

Diethyl 1-methoxy-1-(4-chloro-3-methoxyphenyl)methane phosphonate 4

A solution of dimethyl acetal 3 (4.3 g, 20 mmol), sieve-dried CH$_2$Cl$_2$ (20 ml) and triethyl phosphite (4.1 ml, 24 mmol) was stirred under argon at −78° C. Boron trifluoride ethereats (2.95 ml, 24 mmol) was added dropwise at −78° C., the solution was stirred 5 min and stored overnight at −20° C. The next day the reaction was warmed to room temperature and stirred 5 hours to complete phosphonate formation. With vigorous stirring, the reaction was quenched with solid NaHCO$_3$ followed by 40 ml saturated NaHCO$_3$ solution. After gas evolution ceased, 40 ml CH$_2$Cl$_2$ and 20 ml H$_2$O were added, the biphasic mixture was partitioned and the CH$_2$Cl$_2$ phase was recovered, dried over Na$_2$SO$_4$ and evaporated. After pumping in vacuo, the oil was purified on a silica gel plug, eluting with CH$_2$Cl$_2$ to yield phosphonate 4 as a light yellow oil (6.01 g., 99%).

IR (neat, cm$^{-1}$): 2980, 2930, 1590, 1580, 1480, 1460, 1408, 1280, 1250, 1095, 1055, 1025, 967, 871, 809, 790, 754, 728.

4-Chloro-3-methoxy-1-(methoxy-5-chloro-tricyclo[3,3,1,1$^{3,7}$]dec-2-ylidenemethyl)-benzene 5

Phosphonate 4 (3.2 g, 10 mmol) was dissolved in 30 ml dry THF under argon and cooled to −78° C. Dropwise addition of nBuLi (2.3M, 4.4 ml, 10.1 mmol) generated a yellow-orange phosphonate ylid. After stirring the ylid solution for 10 min, 5-chloro-2 adamantanone (1.75 g, 9.5 mmol), dissolved in 8 ml THF, was added dropwise to the ylid at −78° C. The reaction was slowly warmed to room temperature over 45 min and refluxed for 2 h. Upon cooling, the THF was stripped in vacuo and the product was partitioned between EtOAc/hexanes (1:1) and dilute NaHCO$_3$. The organic layer was dried over NaHCO$_3$. The organic layer was dried over Na$_2$SO$_4$, stripped of solvent and purified on silica gel (2–4% EtOAc/hexanes) to give 3.3 g (96%) of enol ether 5 as a colorless, viscous gum.

4-Chloro-3-hydroxy-1-(methoxy-5-chloro-tricyclo[3.3.1.1$^{3,7}$]dec-2-ylidenemethyl)-benzene 6

Demethylation to enol ether phenol 6 proceeded cleanly upon heating enol ether 5 (3.3 g, 9.3 mmol) in 22 ml DMF at 135° C. in the presence of sodium ethanethiolate (14 mmol) for 1.5 h. The reaction was cooled and partitioned between 50 ml EtOAc, 100 ml 1M NH$_4$Cl and 10 ml saturated NaHCO$_3$ solution. The organic phase was recovered and washed well with water while the aqueous phase was washed once with EtOAc. The EtOAc layers were combined, washed with brine, dried over Na$_2$SO$_4$ and stripped of solvent in vacuo. The crude oil was purified on a silica gel column, eluting with 50% CH$_2$Cl$_2$/hexanes, to give 3.6 g of phenol 6 as a crude oil. Further purification by two crystallizations from a cooled 15% CH$_2$Cl$_2$/hexanes solution provided phenol 6 as a solid (2.18 g, 68%).

IR (CHCl$_3$, cm$^{-1}$): 3530 (OH), 3300 (OH), 2920, 2845, 1568, 1478, 1308, 1190, 1166, 1090, 1079, 1042, 1020, 821.

$^1$H NMR (CDCl3, ppm): 1.57–2.28 (11H, m), 2.75 (1H, br s), 3.27 (3H, s), 3.41 (1H, br s), 5.57 (1H, s), 6.79 (1H, dd, J=8 Hz, 2 Hz), 6.93 (1H, d, J=2 Hz), 7.28 (1H, d, J=8 Hz).

Sodium 2-cyanoethyl 4-chloro-5-(methoxy-(5-chloro)tricyclo[3,3,1,1$^{3,7}$]dec-2-ylidemethyl)-1-phenyl phosphate 7

To a solution of phenol 6 (0.75 g 2.2 mmol), triethylamine (400 µl, 2.86 mmol) and anhydrous THF (8 ml) was added to 2-chloro-2-oxo-1,3,2-dioxaphospholane (Fluka, 240 µl, 2.6 mmol) at room temperature under argon. The reaction was stirred for 3 hours, during which time triethylammonium hydrochloride precipitated out. The reaction solution was pipetted off the precipitate with a cotton-tipped syringe under a strong flow of argon. The precipitate was rinsed several times with ether and the combined solution and rinses were evaporated in vacuo to give a foam, which was protected from exposure to moisture.

The foam was dissolved in anhydrous DMF (4 ml) and stirred with dry NaCN (140 mg, 2.8 mmol) at room temperature for 24 h to form the β-cyanoethyl phosphate diester. The reaction mixture was pumped at high vacuum at 55° C. to remove DMF, leaving phosphate diester 7 as a gum. The crude phosphate diester was photooxygenated without further purification.

Syn- and Anti-disodium 2-chloro-5-(4-methoxyspiro[1,2-dioxetane-3,2,'-(5-chloro-)tricyclo[3,3,1,1$^{3,7}$]-decan]-4-yl)-1-phenyl phosphate 1

Phosphate diester 7 was dissolved in 20 ml 10% MeOH/CHCl$_3$ to which was added 5,10,15,20-tetraphenyl-21H, 23H-porphine (TPP, 0.8 ml of a 2 mg/ml CHCl$_3$ solution). The reaction mixture was saturated with oxygen and irradiated with a 250 W, high pressure sodium vapor lamp wrapped with Kapton film at 5° C. while passing oxygen through the solution. Analytical reverse phase HPLC analysis showed complete dioxetanes formation upon irradiating 20 min. The solvents were stripped in vacuo at room temperature, the residue was pumped to a gum under high vacuum, and stored at –20° C.

The crude cyanoethyl phosphate diester dioxetane 8, dissolved in 11 ml MeOH, was deprotected with sodium methoxide (0.5 ml of 25%, weight NaOMe in MeOH) at room temperature for 30 min. Upon completion of β-elimination of the cyanoethyl group, 2 ml saturated NaHCO$_3$ solution was added and the MeOH was rotory evaporated. HPLC grade water (15 ml) was added and the brown solution was passed through a 0.45μ nylon filter. The solution volume was adjusted to 40 ml with HPLC grade water and purified by preparative HPLC, using a CH$_3$CN/H$_2$O gradient through a polystyrene column (PLRP-S, Polymer Laboratories). The freeze-dried fractions yielded 0.81 g (74% from phenol 6) of dioxetane 1. Analytical reverse phase HPLC on a polystyrene column using a gradient of acetonitrile and 0.1% NaHCO3 and UV detection at 270 nm, showed one peak with a front running shoulder which represented a mixture syn and anti isomers. A sample of the product, as an isomer mixture, was dissolved in a 0.1M diethanolamine buffer (1 mM MgCl$_2$) at pH 10. Upon being treated with alkaline phosphatase, light was emitted as expected, thus confirming the product as a 1,2-dioxetane of the entitled structure.

Chemiluminescent Detection of Alkaline Phosphatase in Solution

Figure 1:
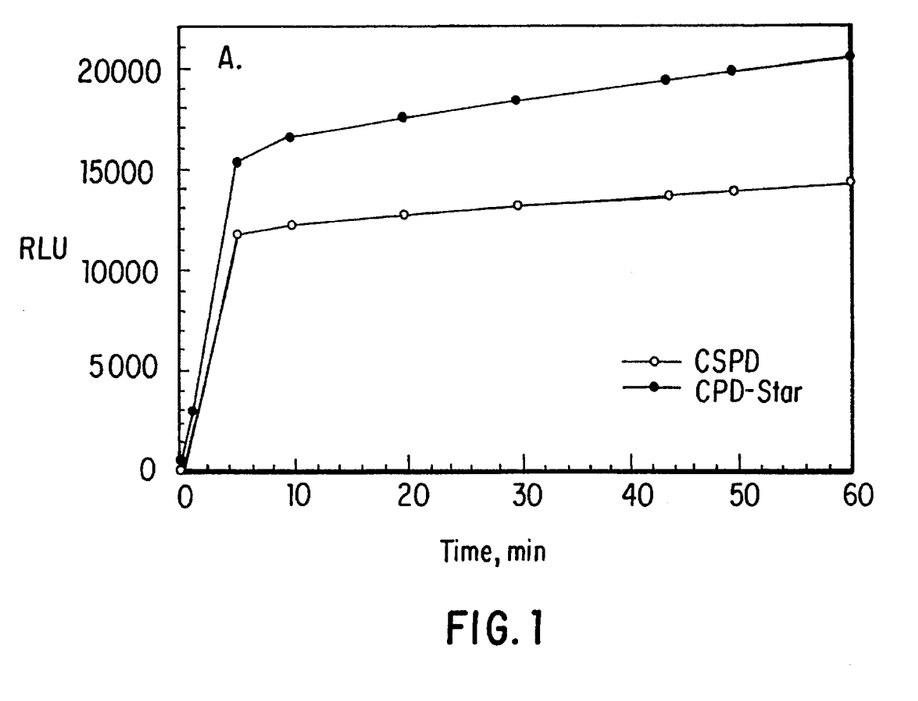
FIGS. 1 and 2 compare the performance of disodium 3(4-methoxyspiro[1,2-dioxetane-3,2'-(5'-chloro)tricyclo [3.3.1.1$^{3.7}$]decan]-4-yl)phenyl phosphate dioxetane (CSPD) with a compound of this invention disodium-2-chloro-5-(4-methoxyspiro[1,2-dioxetane-3,2'(5'-chloro-)tricyclo-{3.3.1.1$^{3,7}$}-decan]-4yl)-phenyl phosphate where the phenyl moiety bears a chlorine substituent at the 4 position (CDP-Star).
Figure 2:
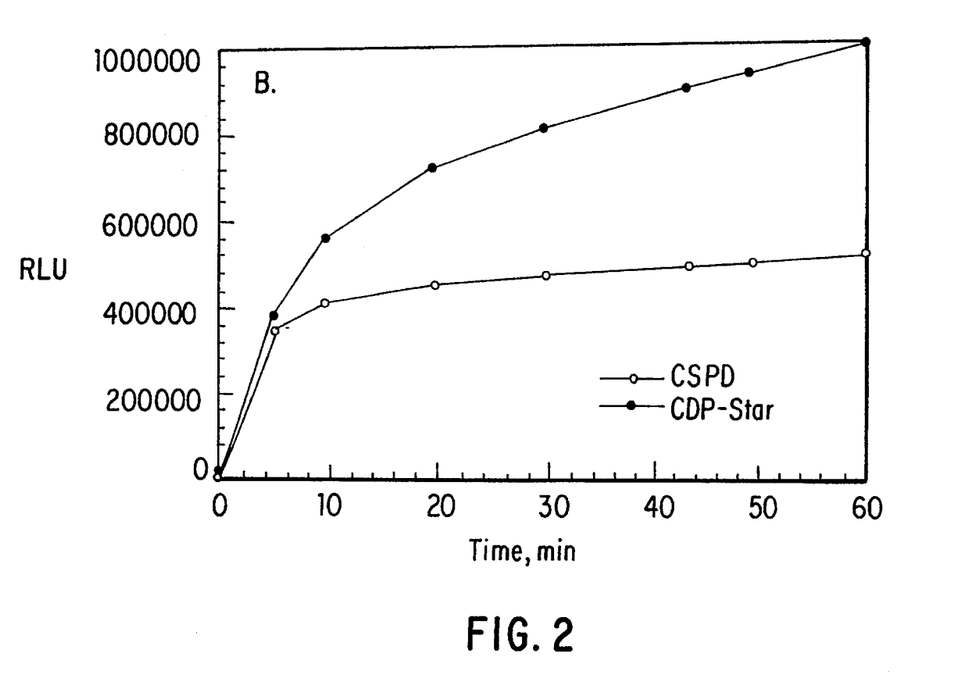

Alkaline phosphatase (5.25×10$^{-17}$ moles) was incubated in 0.5 ml of 0.1M diethanolamine, 1 mM MgCl$_2$, pH 10, containing 0.4 mM dioxetane at room temperature. The chemiluminescence (5 second integral) was measured in a Berthold LB952T luminometer at 5, 10, 20, 30, 44, 50 and 60 minutes. FIGS. 1 and 2 compare the performance of CSPD® and CDP-Star™. FIG. 1 shows the comparison of CSPD® and CDP-Star™ plotted as relative light units (RLU) vs time. The average of three replicates are plotted. FIG. 2 shows the results obtained from another set of samples containing 1 mg/ml of the chemiluminescence enhancing polymer polyvinylbenzyltributylammonium chloride.

Chemiluminescent Detection of Biotinylated pBR322-35mer on Nylon Membrane

Figure 3:
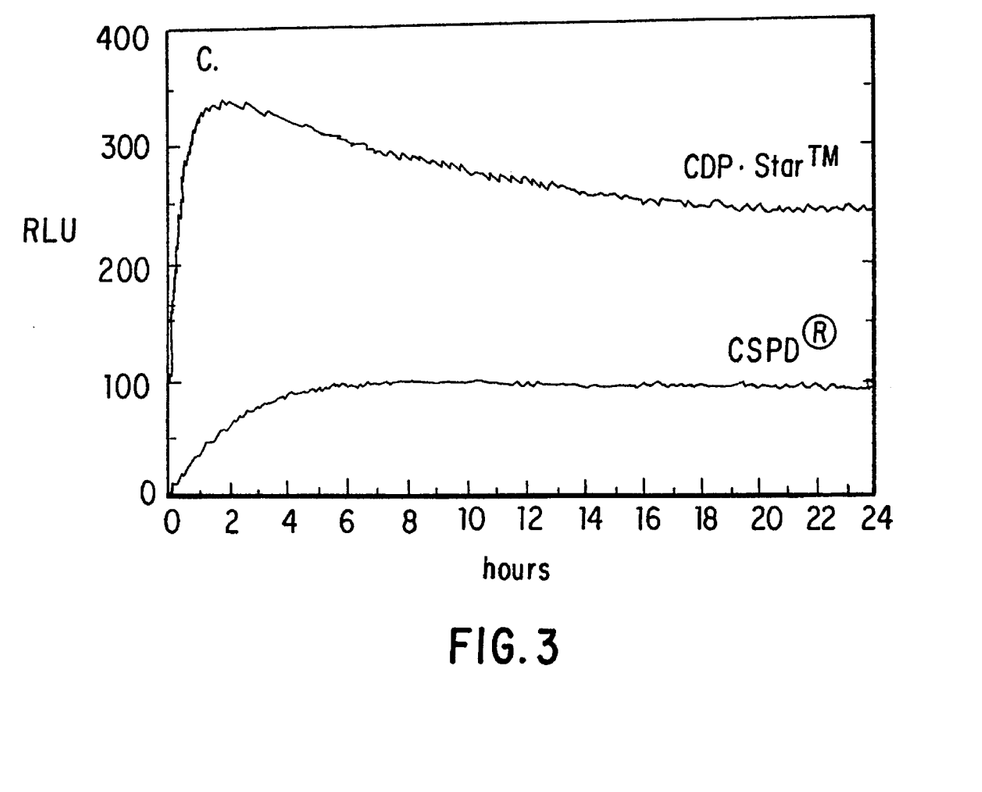
FIG. 3 is a comparison between CSPD and CDP-Star on a nylon membrane assay for biotinylated pBR322-35mer.

Biotinylated pBR322 35-mer (13.1 pg in 1 μl) was spotted onto a small piece of positively charged nylon membrane (Tropilon-Plus™). The membrane was dried completely and DNA was fixed to the membrane by UV cross-linking (120 mJ/cm$^2$). The membrane was wetted with PBS and then incubated in Blocking Buffer (0.2% 1-Block™, 0.5% SDS in PBS) for 10 minutes, in streptavidin-alkaline phosphatase conjugate (Avidx-AP™, Tropix; diluted 1:5000 in Blocking Buffer) for 20 minutes, and washed once for 5 minutes with Blocking Buffer and three times for 5 minute with Wash Buffer (0.5% SDS in PBS). Membranes were then washed twice for 5 minutes with Assay Buffer (0.1M DEA, 1 mM MgCl$_2$, pH 10.0). Finally, membranes were trimmed and sealed in a small square of heat-sealable plastic with 40 μl of 0.25 mM CSPD or CDP-Star (diluted in Assay Buffer). The sealed piece of membrane was immediately taped to a tube (pre-incubated at 22° C.) and placed in a Turner Model 20e luminometer (Turner Designs, Inc. Mountain view, Calif.). Light emission was recorded every 5 minutes, for a period of 24 hrs at 22° C. FIG. 3 is a plot of the chemiluminescence intensity (RLU) vs time for CSPD and CDP-Star.

Chemiluminescent Detection of Western Blotted Human Transferrin

Figure 4A:
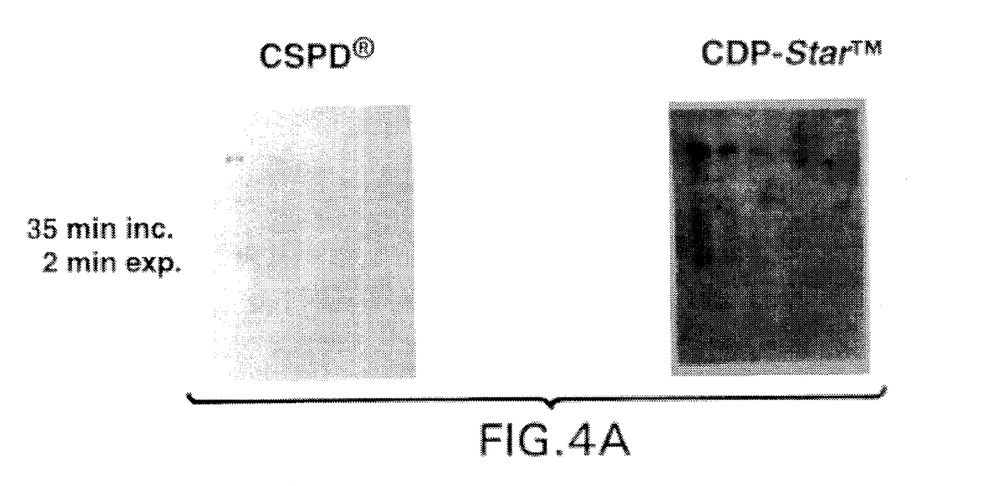
FIGS. 4 and 5 are reproductions of Kodak XAR-5 film exposures of western blotting assays conducted on nylon and PVDF membranes comparing CSPD and CDP-Star.
Figure 4B:
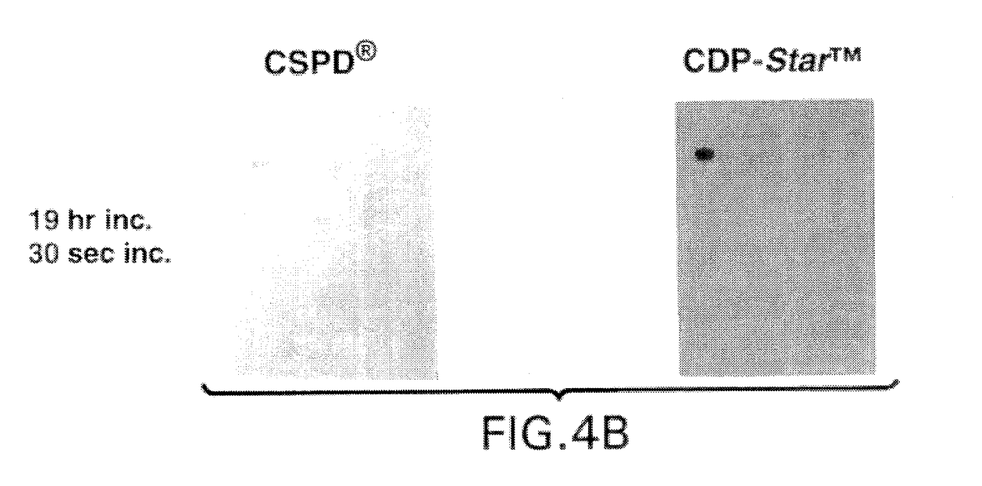
Figure 5A:
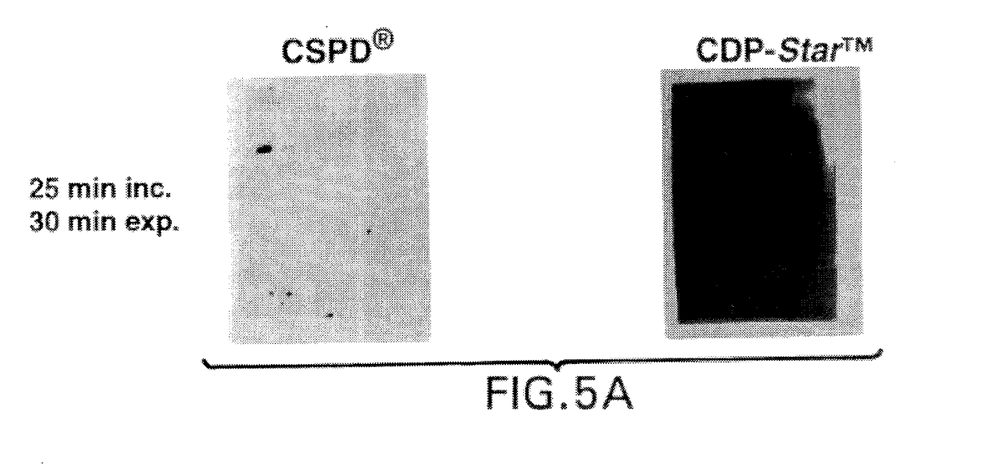
Figure 5B:
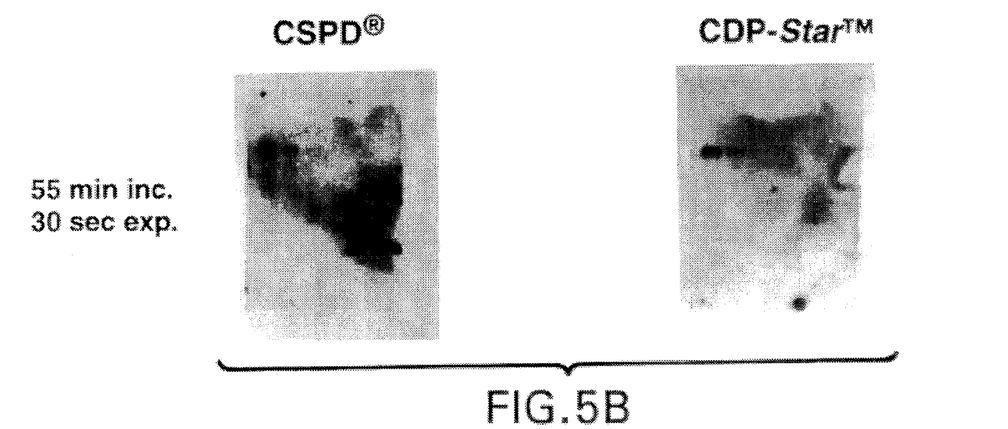

Purified human transferrin (Boehringer Mannheim cat #1317 415) was serially diluted with 1× SDS-PAGE loading buffer (0.06M Tris-HCl, pH 6.8, 2.25% glycerol, 0.5% β-mercaptoethanol, 2% SDS, 0.05% bromophenol blue). Dilutions were heated at 95° C. for 5 minutes and 5 μl of diluted sample was loaded per gel lane. Samples were electrophoretically separated by SDS-PAGE on 10% polyacrylamide minigels, using a Hoefer SE250 minigel apparatus. Each blot contains 10, 3.3, 1.1, 0.37, 0.12 and 0.04 ng amounts of transferrin. Following electrophoresis, gels and membranes were equilibrated with transfer buffer (5 mM MOPS pH 7.5, 2 mM sodium acetate, 20% MeOH) for 15 minutes. Protein was transferred to PVDF (Tropifluor™) and positively charged nylon (Tropilon-Plus™) membrane for 1 hr at 90 V at 4° C. Blots were incubated in Blocking Buffer (BB-1[0.2% 1-Block™, 0.1% Tween-20 in PBS] was used for PVDF and BB-2[3% 1-Block™, 0.1% Tween-20 in PBS] was used for nylon) for 30 minutes. Blots were then incubated with rabbit polyclonal antihuman transferrin (Boehringer/Mannheim cat #615 015; diluted 1:5000 in the appropriate Blocking Buffer) for 30 minutes, and then washed twice for 5 minutes (PVDF with BB-1, and nylon with Wash Buffer [0.1% Tween-20 in PBS]). Next, blots were incubated with goat anti-rabbit IgG alkaline phosphatase conjugate (Tropix; diluted 1:10,000 in the appropriate Blocking Buffer) for 30 minutes, and then washed twice for 5 minutes as above. Blots were then washed twice for 5 minutes in Assay Buffer (0.1M DEA, 1 mM MgCl$_2$, pH 10.0). Finally, blots were incubated with 0.25 mM CSPD or CDP-Star (diluted in Assay Buffer) for 5 minutes. Blots were drained of excess substrate solution, placed in plastic report covers, and exposed to Kodak XAR-5 film. Results obtained on nylon and on PVDF membranes are shown in FIGS. 4–5.

Chemiluminescent Detection of a Single Copy Yeast Gene on Nylon Membrane

Figure 6A:
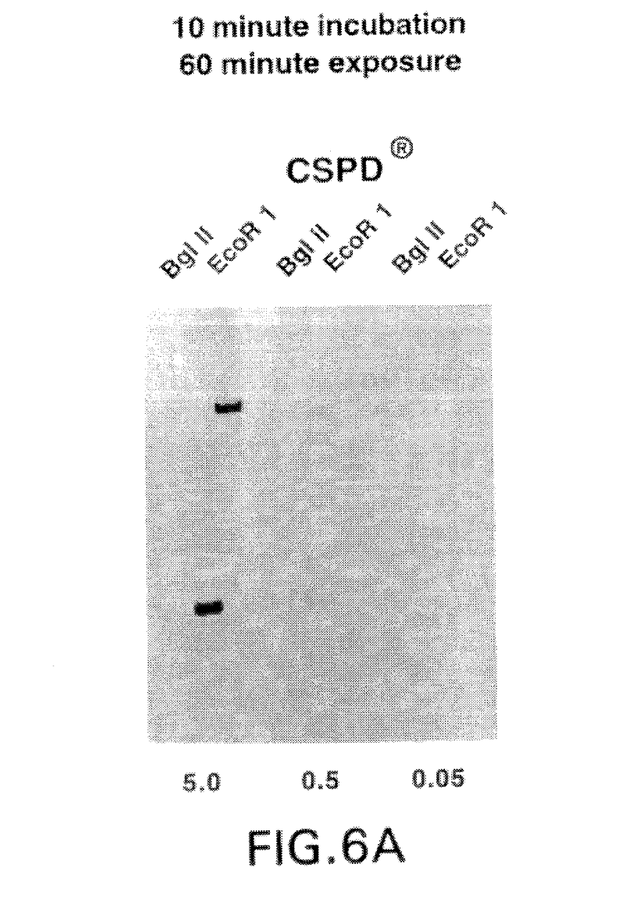
FIGS. 6, 7 and 8 are reproductions of x-ray film contrasting CSPD and CDP-Star incubations of 10 minutes, 70 minutes and 19 hours, respectively, of an assay conducted on nylon membranes for the yeast gene RPB1.
Figure 6B:
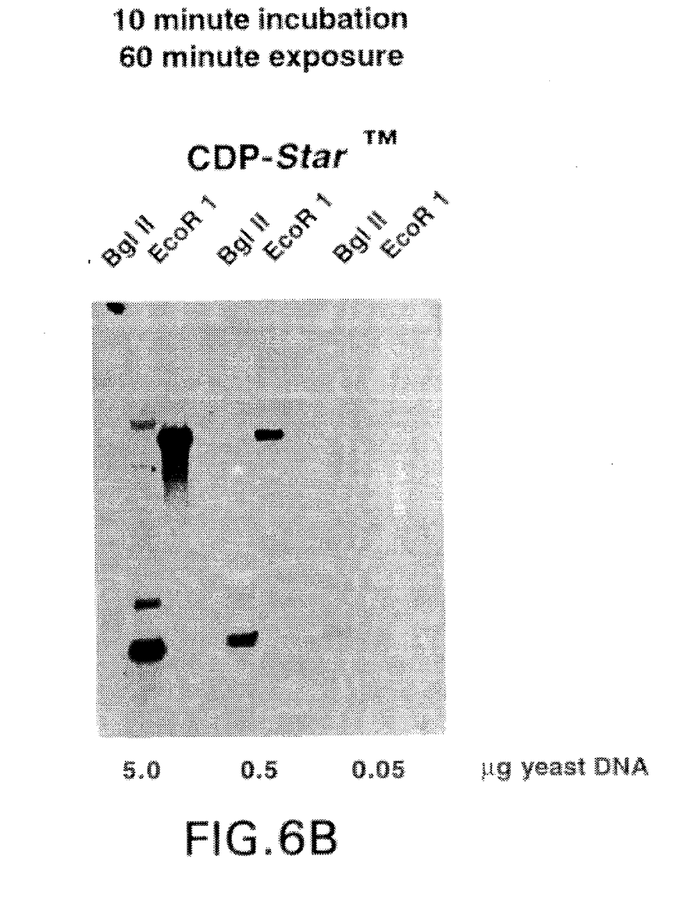
Figure 7A:
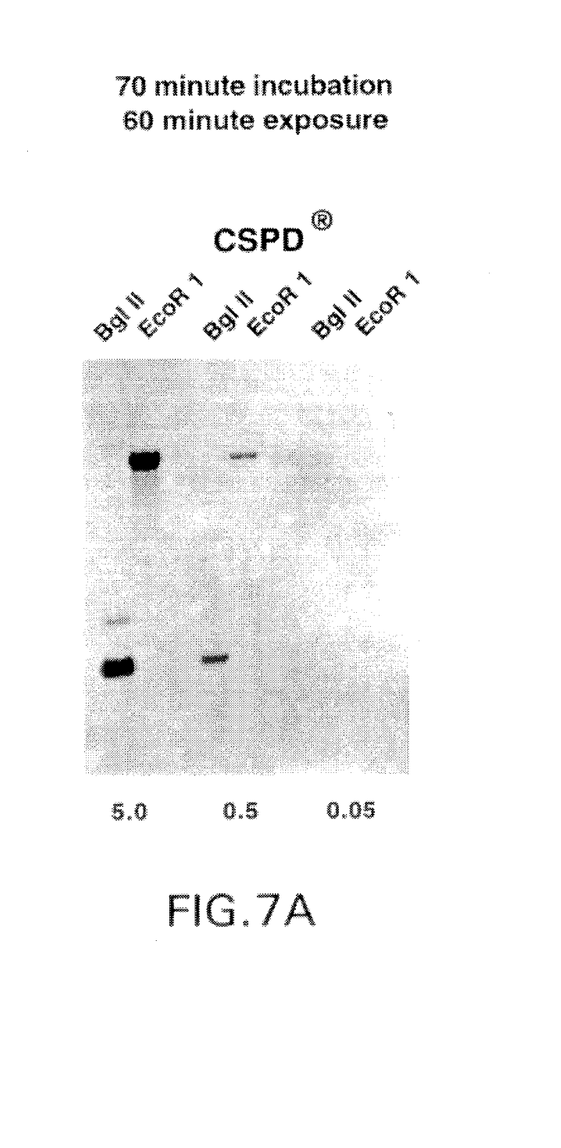
Figure 7B:
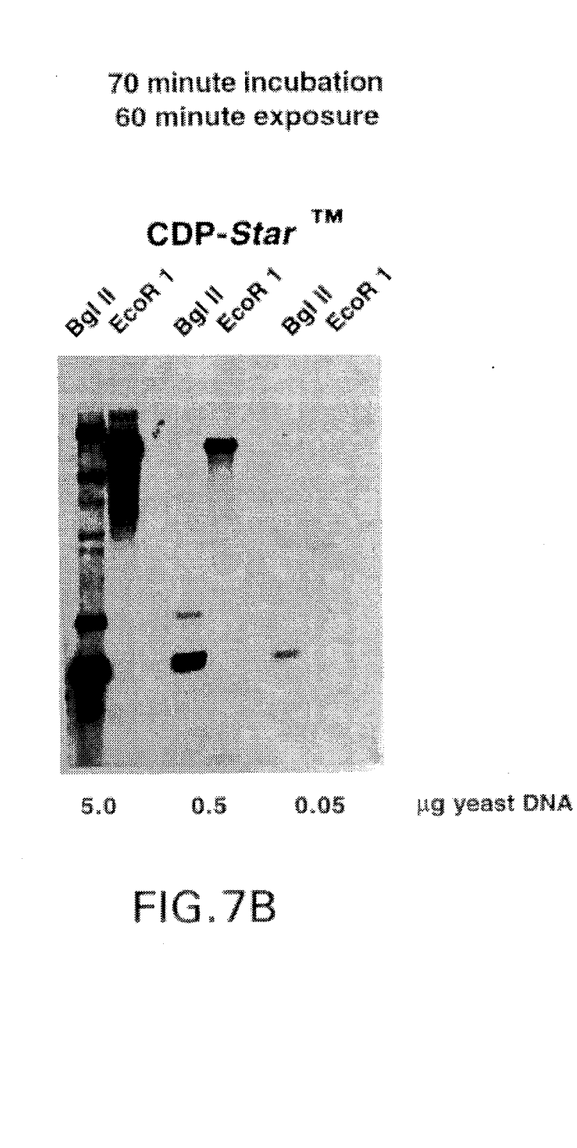
Figure 8A:
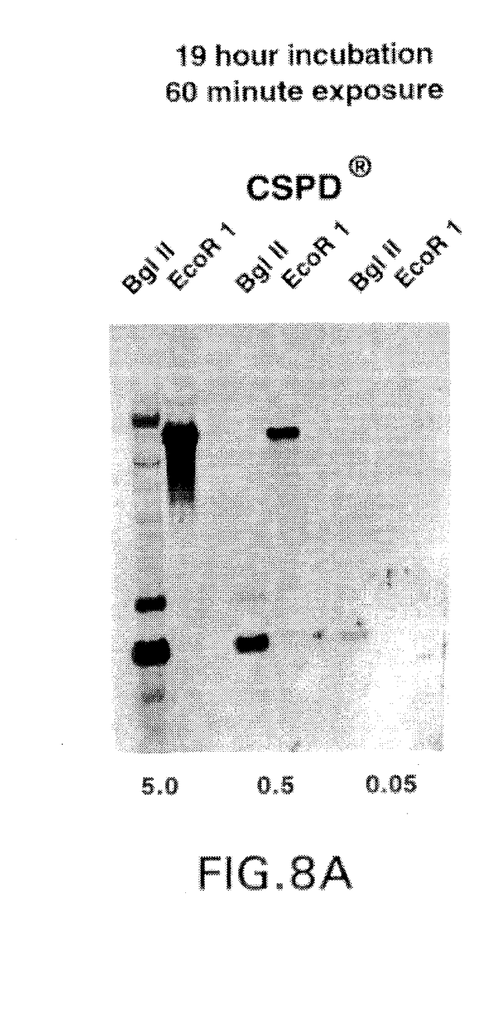
Figure 8B:
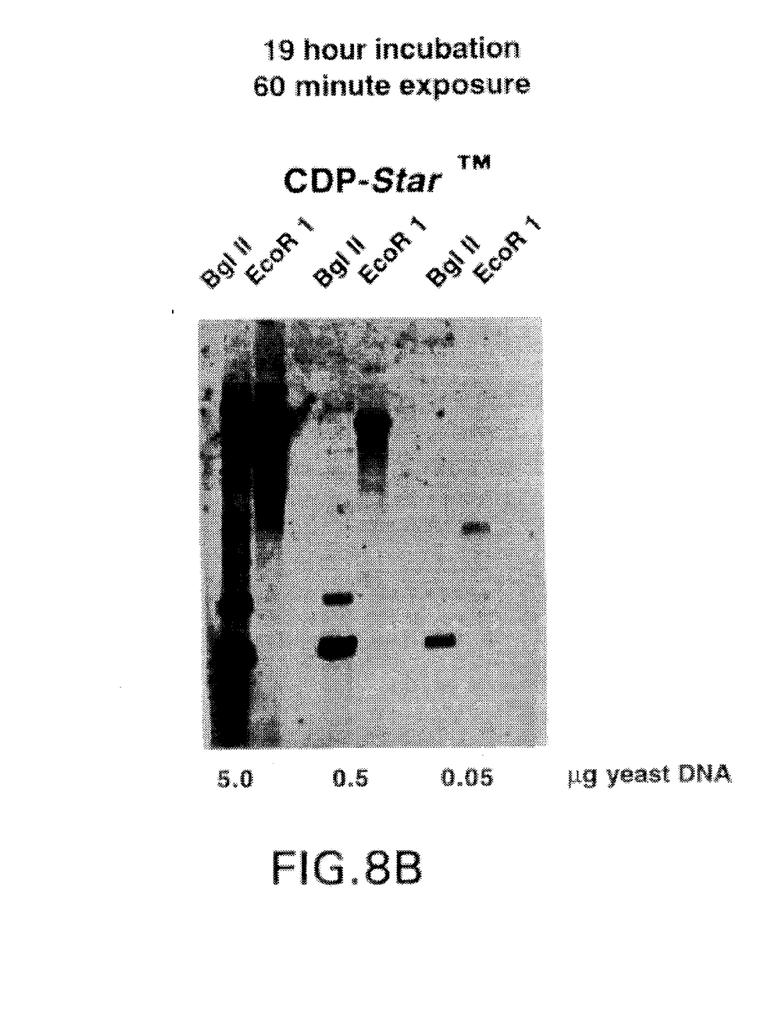

Total genomic DNA from the yeast Saccharomyces cerevisiae was digested with EcoR 1 and Bgl 11 restriction endonucleases. 5.0, 0.5, and 0.05 μg quantities of each DNA digest were separated by electrophoresis in a horizontal 0.8% agarose 1× TBE gel. Following electrophoresis, the gel was soaked in 1.5M NaCl, 0.5M NaOH for 45 minutes to denature the DNA and then incubated in neutralization buffer (1M Tris, 1.5M NaCl, pH 7.4) for 45 minutes. DNA was transferred to positively charged nylon membranes (Tropilon-Plus™) by overnight capillary transfer using 20X SSC. The membranes were air dried and the DNA was UV cross linked to the membranes at 120 mJ/cm². A 1 kb Bgl 11 fragment, excised from the yeast gene RPB 1, was gel purified and biotinylated by a random priming reaction incorporating biotin-14-dCTP. The membranes were prehybridized for 30 minutes at 68° C. in hybridization solution (7% SDS, 0.25M Na$_2$PO$_4$, 1.0 mM EDTA), hybridized overnight at 68° C. with 5 ml of fresh hybridization solution containing 5 ng/ml of denatured probe and then removed from the hybridization solution and washed as follows: twice for 5 minutes with 2× SSC, 1% SDS at room temperature; twice for 15 minutes in 0.1×SSC, 1% SDS at 68° C.; and twice for 5 minutes in 1× SSC at room temperature. The membranes were then incubated for 10 minutes in blocking buffer (0.2% cassein, 0.5% SDS, PBS), and 20 minutes with 1:5000 dilution AVIDx-AP™ in blocking buffer. They were then washed in blocking buffer for 5 minutes, three times for 10 minutes in wash buffer (0.5% SDS, PBS), and twice for 2 minutes in assay buffer (0.1M diethanolamine, 1.0 mM MgCl$_2$, pH 10.0) followed by incubation for 5 minutes in 0.25 mM dioxetane in assay buffer. After draining excess substrate solution, the membranes were wrapped in plastic and exposed to X-ray film. 60 minute exposures taken 10 minutes, 70 minutes, and 19 hours respectively after substrate incubation are reflected in the following exposures. Comparisons of CSDP and CDP-Star are shown in FIGS. 6, 7 and 8.

Chemiluminescent Detection of DNA Sequence Ladders

Figure 9A:
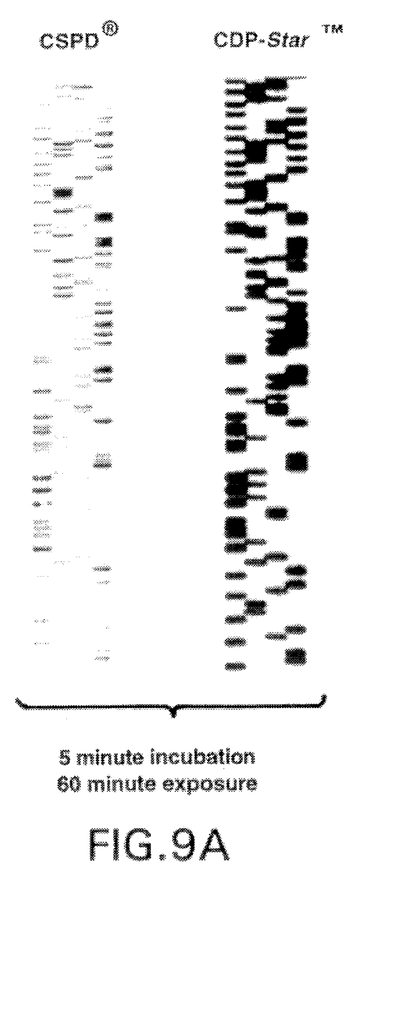
FIG. 9 is a reproduction of x-ray film exposures reflecting chemiluminescent detection of DNA sequence ladders conducted on nylon membranes contrasting CSPD and CDP-Star.
Figure 9B:
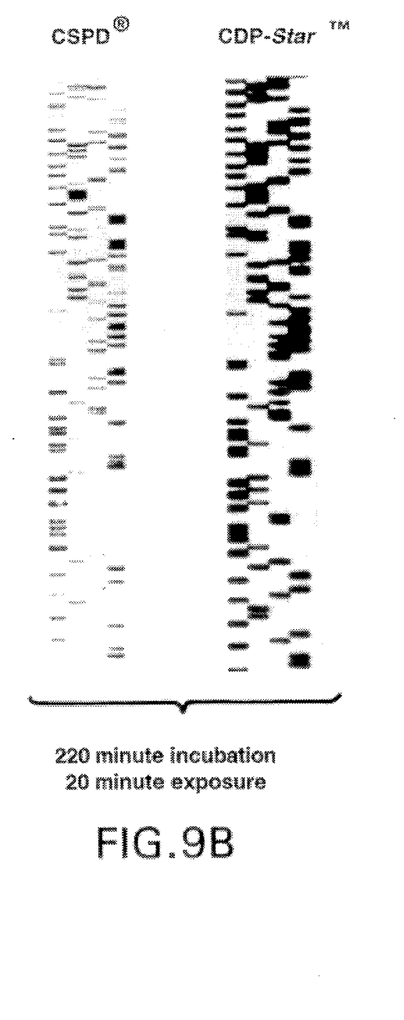
Figure 9C:
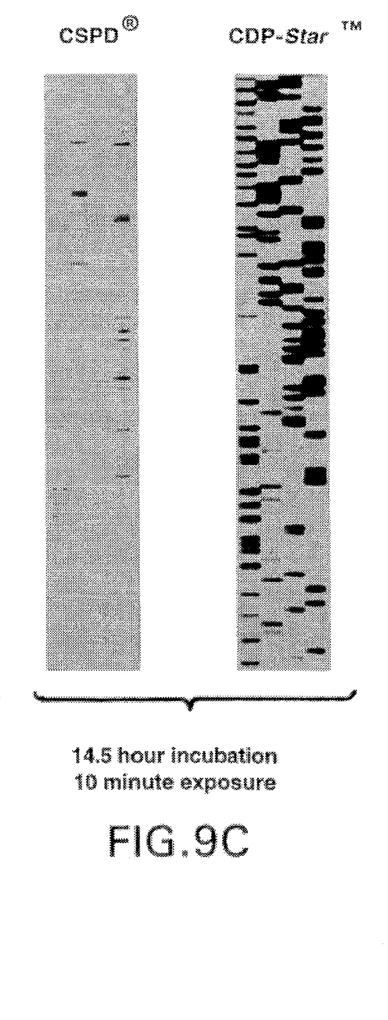

DNA sequencing reactions were performed with the Tropix SEQ-light™ kit using biotinylated (−20) universal primer and single stranded M13 mp18 template DNA. Reaction products were separated on a 6% polyacrylamide 8M urea gel, transferred to Tropilon-Plus™ nylon membranes by capillary action, and UV crosslinked to the membrane (total irradiation-120 mJ/cm²). Chemiluminescent detection was performed by incubating the membrane for 10 minutes in blocking buffer (0.2% i-Block™, 0.5% SDS, PBS), for 20 minutes in conjugate solution (1/5000 dilution of Avidx-AP streptavidin alkaline phosphatase conjugate in blocking buffer), then washing 1×5 minutes with blocking buffer, 3×5 minutes with wash buffer (0.5% SDS, PBS), and 2×2 minutes with assay buffer (0.1M diethanolamine, 1 mM MgCl$_2$, pH 10). Each membrane strip was incubated for 5 minutes with either 0.25 mM CSPD or CDP-Star in assay buffer. All steps were performed at room temperature in a large heat sealed plastic bag with moderate shaking (140–170 rpm). Comparison of CSPD and CDP-Star at three time points is provided. The time after incubation with substrate and exposure time to Kodak XAR-5 x-ray film are indicated on FIG. 9.

This dioxetane can be used for assays of all types in which an enzyme capable of cleaving the dioxetane is present alone or can be attached to one element of the ultimate complex which the analyte, if present, will form. Conventional assay formats are known to those of skill in the art, and are described in the patents set forth above in the Background of the Invention. Exemplary disclosure of suitable assays appears in U.S. Pat. No. 5,112,960, and the same is incorporated herein by reference. The assay format, per se, save for the enhanced performance therein by the dioxetanes of this invention, does not constitute an aspect of the invention.

The dioxetane of this invention, as well as the intermediates therefore, have been disclosed by reference to both generic description and specific embodiment. Additionally, dioxetane performance has been described generally, and exemplified. The examples are not intended as limiting, and should not be construed as such. Variations in substituent identity, and the like, consistent with the disclosure will occur to those of ordinary skill in the art. Such variations and modifications remain within the scope of the invention, save as excluded by the positive limitations set forth in the claims below.

What is claimed is:

1. A dioxetane of the formula

2. A dioxetane of the formula wherein R is Cl-3 alkyl and wherein X is selected from the group consisting of phosphate, galactoside, acetate, 1-phospho-2,3-diacylglyceride, 1-thio-D-glucoside, adenosine triphosphate, adenosine diphosphate, adenosine monophosphate, adenosine, α-D-glucoside, β-D-glucoside, β-D-glucuronide,α-D-mannoside, β-D-mannoside, β-D-fructofuranoside, β-glucosiduranate, P-toluenesulfonyl-L-arginine ester, and P-toluenesulfonyl-L-arginine amide.

3. A method of detecting the presence of alkaline phosphatase in a sample comprising contacting said sample with a dioxetane of claims 1 or 2, and detecting release of light caused thereby, wherein detection of light released indicates presence of alkaline phosphatase in a sample.

4. A method of detecting a first member of a specific binding pair having first and second members, comprising:

optically detecting chemiluminescence produced by the reaction of a dioxetane of claim 1 or 2 with an enzyme which cleaves said enzyme-cleavable group X of said dioxetane, wherein said enzyme is complexed with a second member of said specific binding pair and correlating the chemiluminscene detected with the presence of the first member of said specific binding pair.

5. A kit for conducting a chemiluminescent assay comprising:

a dioxetane of claim 1 or 2, and an enzyme which cleaves the enzyme-cleavable group X of said dioxetane.

6. The kit of claim 4, further comprising a membrane on which said assay may be conducted.

* * * * *

UNITED STATES PATENT AND TRADEMARK OFFICE
CERTIFICATE OF CORRECTION

PATENT NO. : 5,582,980
DATED : December 10, 1996
INVENTOR(S) : Irena Bronstein, et al.

It is certified that error appears in the above-identified patent and that said Letters Patent is hereby corrected as shown below:

Cover Page in the Notice, "Pat. No. 5,326,892" should read -- Pat No. 5,326,882 --.

Cover Page in the Figure, "CPD-Star" should read -- CDP-Star --.

Sheet, Figure 1, "CPD-Star" should read -- "CDP-Star --.

Column 3, line 30, "{3.3.1.1$^{3,7}$]-decan]-4-yl-phenyl" should read -- [3.3.1.1$^{3,7}$]-decan]-4-yl-phenyl --.

Column 4, lines 31-32, "[3,3,1,1$^{3,7}$]-decan]-" should read -- [3.3.1.1$^{3,7}$]-decan]- --.

Column 5, line 64, "tricyclo[3,3,1,1$^{3,7}$]dec-" should read -- tricyclo[3.3.1.1$^{3,7}$]dec- --.

Column 6, line 56, "tricyclo[3,3,1,1$^{3,7}$]dec-" should read -- tricyclo[3.3.1.1$^{3,7}$]dec- --.

Column 7, line 14, "tricyclo[3,3,1,1$^{3,7}$]-decan]-" should read -- tricyclo[3.3.1.1$^{3,7}$]-decan]- --.

Column 8, line 66, "Bgl 11" should read -- Bgl II --.

UNITED STATES PATENT AND TRADEMARK OFFICE
CERTIFICATE OF CORRECTION

PATENT NO. : 5,582,980
DATED : December 10, 1996
INVENTOR(S) : Irena Bronstein, et al.

It is certified that error appears in the above-identified patent and that said Letters Patent is hereby corrected as shown below:

Column 9, line 9, "Bgl 11" should read -- Bgl II --.

Column 9, line 47, "i-Block ™" should read -- I-Block™ --.

Signed and Sealed this

Fourteenth Day of April, 1998

Attest:

*Attesting Officer*

BRUCE LEHMAN

*Commissioner of Patents and Trademarks*